United States Patent
Cross

(10) Patent No.: US 6,534,526 B2
(45) Date of Patent: Mar. 18, 2003

(54) LAMINITIS IN HORSES

(75) Inventor: Dee L. Cross, Central, SC (US)

(73) Assignee: Clemson University, Clemson, SC (US)

(*) Notice: Subject to any disclaimer, the term of this patent is extended or adjusted under 35 U.S.C. 154(b) by 0 days.

(21) Appl. No.: 09/906,386

(22) Filed: Jul. 16, 2001

(65) Prior Publication Data

US 2003/0013738 A1 Jan. 16, 2003

(51) Int. Cl.$^7$ ............................................. A61K 31/445
(52) U.S. Cl. ....................................................... 514/322
(58) Field of Search .......................................... 514/322

(56) References Cited

U.S. PATENT DOCUMENTS

| | | |
|---|---|---|
| 4,005,211 A | 1/1977 | Marsboom |
| 4,066,772 A | 1/1978 | Vanderberk et al. |
| 4,755,519 A | 7/1988 | Dougherty et al. |
| 4,847,243 A | 7/1989 | Wallace |
| 4,880,632 A | 11/1989 | Lipham et al. |
| 5,372,818 A | 12/1994 | Cross et al. |
| 6,224,895 B1 | 5/2001 | Cross |

FOREIGN PATENT DOCUMENTS

| | | |
|---|---|---|
| EP | 0297191 A1 | 1/1989 |
| EP | 0368000 A1 | 5/1990 |

OTHER PUBLICATIONS

Goodman & Gilman's The Pharmacological Basis of Therapeutics, Ninth Edition, (1996), Alpha–Adrenergic Receptor Antagonists, p. 225.*

Effects of Domperidone and Thyroptropin–Releasing Hormone on Secretion of Luteinzing Hormone and Prolactin During the Luteal Phase and Following Induction of Luteal Regression in Sheep, D.R. Deaver et al., Domestic Animal Endocrinology, vo. 4(2):95–102, 1987.

ANotice of Drug Shipment@ forms relative to domperidone for fescue toxicosis in horses, Dee L. Cross, Division of Agriculture and Nature Resources, Clemson University, Jun. 8, 1993.

The Role of Dopamine in the Regulation of Seasonal Reproductive Activity in Mares, Besognet, et al., 28th Meeting of the Society for the Study of Reproduction, Jul. 9–12, 1995.

The Effect of Prepartum and Postpartum Oral Domperidone Therapy on Mares Consuming Endophye–Infested Fescue, Kouba et al., 87th Annual Meeting, Journal of Animal Science, vol. 73, Supplement 1, Jul. 25–28, Orlando, Florida, No year indicated.

Jenner, et al.; "Steroselective actions of substitued benzamide drugs on cerebral dopamine mechanisms"; pp. 39–45; May 17, 1979.

Rossi, et al.; "Pharmacotoxicological Aspects of Levosulpiride"; pp. 81–94: *Pharmacological Research*, vol. 31, No. 2; 1995.

Elliott, et al.; "Substituted Benzamides as Cerebral Dopamine Antagonists in Rodents"; pp. 333–342; *Neuropharmacology*, 1977.

Mizuchi, et al.; "Regional Distribution of Sultopride and Sulpride in Rat Brain Measured by Radioimmunoassay"; pp. 195–198; *Psychopharmacology*, 1983.

de Munain, et al.; "Tardive Akathisia Due to Sulpiride"; pp. 481–783; *Clinical Neruropharmacology*; vol. 17, No. 5; 1994.

Martensz, et al.; "Drug–Induced Hyperprolactinaemia and Discharges of Luteinizing Hormone Evoked By Oestrogen in Ovariectomized Rhesus Monkeys"; pp. 111–122; *Journal of Endocrinology*; 1982.

Massara, et al.; "Increased thyrotrophin and prolactin secretion induced by domperidone in hypothyroid subjects"; pp. 48–53. No year indicated.

Ferrari, et al.; "Behavioural Evidence for Central D–2 Dopamine Receptor Agonistic Effect by Some 2–(Fluorohydroxphenyl)Ethylamines"; pp. 131–134; *Pharmacology Biochemistry & Behavior*, vol. 38; 1991.

European Journal of Obstretrics, Gynocology and . . . ; pp. 283–287; vol. 19, No. 5, May, 1985.

"Dopaninergic regulation Of Gonadotrophin Secretion In Seasonally Anoestrous Mares", B. Besonet, et al., *Journal Of Reproduction And Fertility* (1996) 108, pp 55–61.

JICST—EPlus Abstracts, 1999, Shiegemi, et al., AN 950481355.

BIOSIS Abstracts, 1995: 101711, Litherland, A.J. , et al.

Minireview, "The Pharmacology Of Sulpiride—A Dopamine Receptor Antagonist", S.E. O'Connor, et al., *General Pharmacology*, 1982, 13/3, pp 185–193.

"Systemic Sulpiride Increases Dopamine Metablites In The Lateral Hypothalamus", T. Baptista, et al., *Pharmacology Biochemistry And Behavior*, 1990, vol. 37, pp. 227–229.

Entry #3476 The Merck Index, Twelfth Ed., 1996, p. 578.

Robert J. Hunt, DVM, MS Continuing Education Article #9 "The Pathophysiology of Acute Laminitis", vol. 13, No. 6, Jun. 1991.

(List continued on next page.)

Primary Examiner—Dwayne C. Jones
Assistant Examiner—C. Delacroix-Muirheid
(74) Attorney, Agent, or Firm—Dority & Manning

(57) ABSTRACT

The present invention generally relates to various methods for treating the laminitis syndrome in animals. These benefits are obtained by administering to the animals a composition containing an α-adrenergic antagonist that does not substantially cross the blood brain barrier. In one embodiment, the α-adrenergic antagonist is domperidone. The domperidone can be administered to the animal either orally, subcutaneously, or intramuscularly and can be used to treat animals suffering from symptoms of laminitis.

33 Claims, No Drawings

OTHER PUBLICATIONS

J. Warren Evans, Horses—Second Edition—"A Guide to Selection, Care and Enjoyment", W.H. Freeman & Company, New York, pp 263–268. No year indicated.

Liz Newall, "Home to Invention," p. 21, Clemson World/Spring 1999.

Marci Campbell "More Milk, Please". The Quarter Horse Journal, Mar. 1996, p. 63.

Nancy J. Lane "Morphology of Glial Blood–brain Barriers". No year indicated.

Annals New York Academy of Science—pp348–362.

Magnus Bundgaard and Helen F. Cserr "Barrier Membranes At The Outer Surface Of The Brian Of An Elasmobranch, Raja erinacea". Cell and Tissue Research—Spring Edition 1991.

* cited by examiner

LAMINITIS IN HORSES

BACKGROUND OF THE INVENTION

Laminitis is a potentially devastating condition which can strike any hoofed animal, but is primarily known to affect equine. Generally speaking, laminitis is a syndrome involving the sensitive laminae of the hoof. The lamina is a layer of loose connective tissue attaching the distal phalanx to the hoof wall.

The syndrome can proceed through several stages, beginning with little or no visible signs of the disease, though lamellar damage may have already occurred at this point. Once begun, if unchecked, the condition can advance to a chronic stage, which can involve detachment of the lamina from the hoof and palmar rotation or even distal displacement of the bone. At the chronic stage, a horse can be left with continuous mild or severe pain which can last indefinitely. It is generally held that the laminitis syndrome is responsible for the permanent debilitation of countless horses every year, affecting all breeds around the world.

While the pathophysiology of the syndrome has gained understanding in recent years, attempts at treatment and prevention of the disease have met with limited success. In the past, treatment was limited to physical treatment of the affected foot, by, for example, minimizing movement by standing the horse in a deep (18 inch) bed of shavings, or fitting special frog supports for the animal. Chemical treatment of symptoms has also been utilized in the past, such as administration of phenylbutazone for inflammation and pain.

More recently, studies have shown that laminitis may begin as a primary vascular disease, and treatment methods have focused on vascular control mechanisms. For example, it has been proposed that digital venoconstriction may be the primary disturbance occurring in the initial stages of laminitis. As a result, certain substances have been examined that may interrupt this process. For example, certain catecholamine antagonists have been examined for possible efficacy. Catecholamines are believed to be mediators in the hormone cascade which can lead to vascular constriction. Specifically, certain α-adrenergic antagonists have been examined as possible agents for inhibiting suspected hormone cascades which can lead to the vasoconstriction found in early laminitis. Success has been limited, however. For example, the α-adrenergic antagonist phenoxybenzamine has been associated with side effects such as hypotension, recumbency, and a prolonged duration of action. Similarly, when the α-adrenergic antagonist acepromazine maleate has been examined, undesirable side effects such as sedation and cholinesterase inhibition can occur in the animal.

In spite of the recent advances in understanding the development of laminitis, specific hormone cascades and possible mediators to the vasoconstriction remain unsubstantiated. Successful treatment of the syndrome remains frustratingly infrequent and uncertain. The present invention is related to a method for treating laminitis and preventing the damage which has been known to occur in the chronic stages of the disease.

SUMMARY

In general, the present invention is directed to a method for treating laminitis in animals. More specifically, the present invention is directed to a method for treating the symptoms associated with the laminitis syndrome.

When laminitis proceeds to a chronic stage, laminar detachment can occur, which in turn can lead to palmar rotation and/or vertical displacement of the distal phalanx. The method of the present invention, properly administered, can prevent this laminar detachment.

Laminitis is believed to be due to microcirculatory system impairment. The method of treatment of the present invention includes administering to an animal suffering laminitic symptoms a composition which includes an α-adrenergic antagonist. The α-adrenergic antagonist chosen for treatment is preferably one which does not cross the blood-brain barrier, thus allowing treatment without neuroleptic side effects. In one particular embodiment, the α-adrenergic antagonist can be domperidone.

The α-adrenergic antagonist used for treatment of the animal can be administered to the animal by any suitable method. For example, the α-adrenergic antagonist can be administered to the animal orally, subcutaneoously, or intramuscularly. Generally, the α-adrenergic antagonist will be administered to the animal in an amount from about 0.2 mg to about 3.3 mg per kg weight of the animal. When the treatment is administered to the animal subcutaneously or intramuscularly, the dosage can be, for example, from about 0.08 mg to about 1.32 mg per kg weight of the animal. Administration of treatment can occur at least once per day up to about six times per day (every four hours).

Lamellar damage due to laminitis is known to occur primarily in horses, but it can occur in any hoofed animal. The treatment of the present invention is therefore equally efficacious for other hoofed animals, such as, for example, cattle, camels, goats, pigs, and sheep.

Other objects, features and aspects of the present invention are discussed in greater detail below.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is generally directed to treatment of laminitis in hoofed animals. More particularly, the present invention is directed to various processes and methods for treating laminitis and prevention of lamellar damage due to laminitis in animals. The process of the present invention can be used either as a prophylactic for laminitis in hoofed animals or alternatively as a treatment for laminitis after physical manifestations of the disease have appeared. In fact, experimental trials of the treatment have led to long term elimination of any signs of the disease as well as speculation of no return of symptoms in the future.

In general, the objects and advantages of the present invention are achieved by administering to a laminitic animal a composition containing an α-adrenergic antagonist. Preferably, an α-adrenergic antagonist should be chosen that does not substantially cross the blood-brain barrier in order to minimize the possibility of the animal suffering adverse behavioral or neurological side effects. For instance, in a preferred embodiment, the α-adrenergic antagonist is domperidone.

Domperidone is the common name for the compound 5-Chloro-1-[1-[3-(2,3-dihydro-2-oxo-1H-benzimidazol-1-yl)propyl]-4-piperidinyl]-1,3-dihydro-2H-benzimidazol-2-one. Domperidone is registered under the Chemical Abstact Service registration system and has been assigned registry number 57808-66-9. Domperidone is chemically unrelated to other α-adrenergic antagonists, such as phenoxybenzamine and acepromazine maleate. Unlike other α-adrenergic antagonists, domperidone does not cross the blood brain barrier. Therefore, central neurological side effects are not a concern when using domperidone as a treatment for laminitis.

Although a great deal of the pathophysiology of laminitis remains unknown, current research suggests it to be a microcirculatory problem. Current research suggests that prior to lamellar damage, an as yet unknown hormone cascade causes blood vessels to constrict in the distal digit of the animal. It is believed that this constriction involves both pre-capillary bed vessels (arterioles) as well as post-capillary bed vessels (venules). In any case, it is generally held that flow of blood to and/or from the laminar capillaries is impeded in the earliest stages of the disease.

Vasoconstriction which impedes the blood flow in the hoof can cause edema in the surrounding tissues. This in turn can lead to an increase in interstitial pressure which can further impede circulation. The net effect, if left unchecked, can lead to ischemia of the surrounding tissues (including the dermal laminae), formation of thromboses in the vessels, and formation of arteriovenous shunts around the effected area, which further deplete the blood supply to the hoof.

If the disease continues to advance, necrosis of the affected tissue can begin. Sufficient tissue damage can lead to detachment of the laminae from the hoof wall, at which point the phalanx can rotate and/or become vertically displaced within the hoof.

Although the specific hormone cascade which is believed to initiate laminitis is unknown, it is believed to involve catecholamines. Catecholamines are known vasoconstrictive substances and are believed to be intermediaries in the development of laminitis.

In accordance with the present invention, the inventor has discovered that domperidone, properly administered, is a safe and effective treatment for laminitis. Although the specific biological process is unknown, it is believed that domperidone acts as an α-adrenergic antagonist and interferes with the hormone or neurotransmitter cascade with activation of receptors, which can lead to the initial vasoconstriction occurring in the syndrome.

The process of the present invention can be used to treat any animal suffering similar lamellar damage, but is particularly applicable to livestock. For instance, many problems have been experienced due to laminitis in equine, but laminitis exists in other animals as well, such as for example bovine, pigs, sheep, camels, and any other hoofed animal. The disclosed treatment can be used for any laminitic animal.

According to the present invention, the vasoconstriction which is believed to be one of the primary disturbances in early laminitis is inhibited by administering to an animal an α-adrenergic antagonist. In one preferred embodiment, the α-adrenergic antagonist is domperidone. The α-adrenergic antagonist can be administered to the animal in any suitable procedure. For example, the α-adrenergic antagonist can be administered orally, as a subcutaneous injection, as an intramuscular injection, or as a suppository.

In one embodiment, when treating with domperidone, it has been found that laminitic symptoms can be treated when the domperidone is taken orally by an animal in an amount of from about 0.2 mg/kg (mg of domperidone per kg of body weight) to about 3.3 mg/kg. At concentrations greater than 3.3 mg/kg, no further benefits have been observed. Thus far, the best results have been obtained when domperidone has been taken orally at concentrations of about 1.1 mg/kg.

If domperidone is injected subcutaneously or intramuscularly into the animal, the dosages listed above can be reduced to about 40% of the oral dose. Thus, if injected into an animal, domperidone can be administered at a concentration of from about 0.08 mg/kg to about 1.32 mg/kg, with a preferred concentration of about 0.44 mg/kg.

Frequency of administration of the α-adrenergic antagonist can vary from case to case and animal to animal. In general, when treating laminitic symptoms in horses by administration of domperidone, the composition has been found to be effective when administered to the animal at the recommended concentrations at least once per day. In certain embodiments, however, it may be desired to administer the treatment to an animal more often. For example, in some cases, the desired dosage may be administered to an animal about every four hours, or six times per day.

Treatment can begin at the first signs of laminitis. Such signs can include but are not limited to: a pounding digital pulse from the digital artery on either side of the fetlock, pain in the feet, lameness, shifting weight between the feet, hot hooves, standing on the heels, reluctance to move, depression around the coronary band, or frequent lying down. Generally, treatment will continue for several days beyond the termination of symptoms. Should symptoms return, treatment can be reinstituted.

Although unknown, it is believed that α-adrenergic antagonists, such as domperidone, block vasoconstrictor activity within the animal. Domperidone is believed to block α-adrenergic receptors thus neutralizing the effect of certain vasoconstrictive hormones or neurotransmitters like the catecholamines that are believed to be mediators in the hormone cascade leading to the vasoconstriction found in early laminitis.

In general, in delivering an effective dosage of an α-adrenergic antagonist to an animal according to the present invention, various vehicles may be used. For instance, when taken orally, the α-adrenergic antagonist may be combined with a feed or feed supplement material, a suitable oral gel or any other suitable carrier. If injected, the drug may be mixed with any suitable carrier. Additionally, the α-adrenergic antagonist may be added to salt blocks or mineral blocks during casting or mixed directly into feed. Further, various other administration techniques well known in the art may be employed. It is to be understood that the present invention is not to be limited to any particular vehicle.

It also should be appreciated that although the above description and following examples relate primarily to horses, it is believed that the drug will work as described with any animal.

The present invention may be better understood with reference to the following examples.

EXAMPLE NO. 1

A 15 year old Arabian mare was treated which had been laminitic for approximately 2 years. The mare had been diagnosed by a veterinarian with chronic founder. Domperidone was orally administered at 1.1 mg/kg twice a day for 15 days. After three days of treatment, laminitic symptoms had disappeared. The mare remained sound for at least 15 days. A few weeks later, treatment was resumed after return of symptoms. After four days of treatment, the mare was sound again. Laminitic symptoms did not return. There were no side effects noted during treatment.

EXAMPLE NO. 2

A pony of approximately 400 pounds was diagnosed with laminitic founder due to grain overload. Domperidone was orally administered at 1.1 mg/kg twice per day. No other medication was administered. The pony was walking the second day of treatment with no apparent stiffness. Treatment was continued for an additional two days. Complete recovery was apparent.

EXAMPLE NO. 3

Two horses showing early signs of laminitis were treated with domperidone at 1.1 mg/kg orally, twice per day. Symptoms were gone in both animals after two days of treatment. Total treatment lasted 5 days. No return of symptoms was noted.

EXAMPLE NO. 4

A recently obtained mare began showing signs of laminitis a few days after purchase. The laminitic symptoms remained for several weeks before treatment was attempted. The mare was treated orally with domperidone at 1.1 mg/kg, SID for 5 days. After three days of treatment, the mare was showing no signs of laminitis. The mare fully recovered.

EXAMPLE NO. 5

A horse showing signs of lameness of an unknown etiology was treated with domperidone. Domperidone was administered orally, 1.1 mg/kg, SID for 5 days. The laminitic symptoms disappeared after the second day of treatment and did not return.

EXAMPLE NO. 6

A Paso Fino mare which normally had a fairly hyperactive temperament and had shown no previous signs of lameness, had been off of her feet for two days prior to treatment commencing. At the time, the mare was receiving 2 pounds of shelled corn per day plus winter pasture. Examination revealed a pounding digital pulse in all four feet, and the mare would not walk even with prodding or slapping on her rear quarters. Treatment was commenced which included 1.1 mg/kg domperidone administered orally twice a day, banamine, plus acepromazine. By the afternoon of the second day of treatment, the mare had improved and was walking some on her own, without prodding. After ten days of treatment, the mare was about 75% improved.

These and other modifications and variations to the present invention may be practiced by those of ordinary skill in the art, without departing from the spirit and scope of the present invention, which is more particularly set forth in the appended claims. In addition, it should be understood that aspects and various embodiments may be interchanged both in whole or in part. Furthermore, those of ordinary skill in the art will appreciate that the foregoing description is by way of example only, and is not intended to limit the invention so further described in such appended claims.

What is claimed is:

1. A method for treating the laminitis syndrome comprising:
   administering to an animal in need thereof a composition comprising an α-adrenergic antagonist that does not substantially cross the blood-brain barrier, said α-adrenergic antagonist comprising domperidone, said α-adrenergic antagonist being administered to said animal in an amount sufficient to treat the laminitis syndrome.

2. A method as defined in claim 1, wherein said α-adrenergic antagonist is administered to said animal in an amount from about 0.08 milligrams to about 3.3 milligrams per kg weight of said animal.

3. A method as defined in claim 1, wherein said composition is administered orally.

4. A method as defined in claim 1, wherein said composition is administered subcutaneously.

5. A method as defined in claim 1, wherein said composition is administered intramuscularly.

6. A method as defined in claim 1, wherein said domperidone is administered to said animal orally in an amount from about 0.2 milligrams to about 3.3 milligrams per kilogram weight of said animal.

7. A method as defined in claim 1, wherein said domperidone is administered to said animal subcutaneously in an amount from about 0.08 milligrams to about 1.32 milligrams per kilogram weight of said animal.

8. A method as defined in claim 1, wherein said domperidone is administered to said animal intramuscularly in an amount from about 0.08 milligrams to about 1.32 milligrams per kilogram weight of said animal.

9. A method as defined in claim 1, wherein said composition is administered to said animal at least once a day.

10. A method as defined in claim 1, wherein said composition is administered to said animal between about once and about six times each day.

11. A method as defined in claim 1, wherein said animal is a horse.

12. A method as defined in claim 1, wherein said animal is selected from the group consisting of horses, cattle, camels, goats, pigs, and sheep.

13. A method for preventing laminar detachment due to laminitis comprising:
    administering to an animal in need thereof a composition comprising an α-adrenergic antagonist that does not substantially cross the blood-brain barrier, said α-adrenergic antagonist comprising domperidone, said domperidone being administered to said animal in an amount sufficient to prevent laminar detachment due to laminitis.

14. A method as defined in claim 13, wherein said domperidone is administered to said animal in an amount from about 0.08 milligrams to about 3.3 milligrams per kg weight of said animal.

15. A method as defined in claim 13, wherein said composition is administered orally.

16. A method as defined in claim 13, wherein said composition is administered subcutaneously.

17. A method as defined in claim 13, wherein said composition is administered intramuscularly.

18. A method as defined in claim 16, wherein said domperidone is administered to said animal orally in an amount from about 0.2 milligrams to about 3.3 milligrams per kilogram weight of said animal.

19. A method as defined in claim 16, wherein said domperidone is administered to said animal subcutaneously in an amount from about 0.08 milligrams to about 1.32 milligrams per kilogram weight of said animal.

20. A method as defined in claim 17, wherein said domperidone is administered to said animal intramuscularly in an amount from about 0.08 milligrams to about 1.32 milligrams per kilogram weight of said animal.

21. A method as defined in claim 13, wherein said composition is administered to said animal at least once a day.

22. A method as defined in claim 13, wherein said composition is administered to said animal between about once and about six times each day.

23. A method as defined in claim 13, wherein said animal is a horse.

24. A prophylactic or treatment method for blocking receptor activity in a hoofed animal to prevent digital laminar detachment due to microcirculatory system impairment comprising:

administering to the hoofed animal a composition comprising domperidone, said domperidone being administered to said hoofed animals in an amount from about 0.08 milligrams to about 3.3 milligrams per kg weight of said hoofed animal.

25. A method as defined in claim 24, wherein said composition is administered orally.

26. A method as defined in claim 24, wherein said composition is administered subcutaneously.

27. A method as defined in claim 24, wherein said composition is administered intramuscularly.

28. A method as defined in claim 25, wherein said domperidone is administered to said hoofed animal orally in an amount from about 0.2 milligrams to about 3.3 milligrams per kilogram weight of said hoofed animal.

29. A method as defined in claim 26, wherein said domperidone is administered to said hoofed animal subcutaneously in an amount from about 0.08 milligrams to about 1.32 milligrams per kilogram weight of said hoofed animal.

30. A method as defined in claim 27, wherein said domperidone is administered to said hoofed animal intramuscularly in an amount from about 0.08 milligrams to about 1.32 milligrams per kilogram weight of said hoofed animal.

31. A method as defined in claim 24, wherein said composition is administered to said hoofed animal at least once a day.

32. A method as defined in claim 24, wherein said composition is administered to said hoofed animal between about once and about six times each day.

33. A method as defined in claim 24, wherein said hoofed animal is a horse.

* * * * *